US 6,699,039 B2

(12) United States Patent
Dryer (10) Patent No.: US 6,699,039 B2
(45) Date of Patent: Mar. 2, 2004

(54) VERSATILE SYSTEM FOR MANIPULATION OF DENTAL APPLIANCES

(75) Inventor: Jeff Dryer, Allen, TX (US)

(73) Assignee: Dryer Pliers, Inc., Plano, TX (US)

( * ) Notice: Subject to any disclaimer, the term of this patent is extended or adjusted under 35 U.S.C. 154(b) by 0 days.

(21) Appl. No.: 10/156,596

(22) Filed: May 28, 2002

(65) Prior Publication Data

US 2003/0224323 A1 Dec. 4, 2003

(51) Int. Cl.[7] .................................................. A61C 3/14
(52) U.S. Cl. ...................................................... 433/159
(58) Field of Search .......................... 433/39, 40, 159, 433/2, 3

(56) References Cited

U.S. PATENT DOCUMENTS

| | | | | |
|---|---|---|---|---|
| 1,518,021 A | * | 11/1924 | Truxillo | 433/159 |
| 2,698,483 A | * | 1/1955 | Berkowitz | 433/156 |
| 3,713,222 A | * | 1/1973 | Tofflemire | 433/159 |
| 4,197,647 A | | 4/1980 | Goldenthal | 433/159 |
| 5,195,889 A | * | 3/1993 | von Weissenfluh | 433/40 |
| 5,839,896 A | | 11/1998 | Hickok et al. | 433/159 |
| 6,095,815 A | * | 8/2000 | Mueller | 433/159 |
| 6,142,781 A | | 11/2000 | Fischer | 433/149 |
| 6,322,363 B1 | | 11/2001 | Beecher et al. | 433/159 |
| 6,431,864 B1 | * | 8/2002 | Silverstein | 433/159 |
| 2002/0106609 A1 | * | 8/2002 | Palermo et al. | 433/159 |

OTHER PUBLICATIONS

Matrix Band Forceps advertisement, p. 3 of PracticonDental's Fall 2002 Catalog.
Matrix Band Forceps advertisement, p. 1 of Aug., 2002 Dental Products Report.

* cited by examiner

Primary Examiner—Cary E. O'Connor
(74) Attorney, Agent, or Firm—Ronald W. Burns (57) ABSTRACT

A versatile system for the manipulation of dental appliances is described that includes a grasping assembly coupled to an actuating assembly. Members of the grasping assembly are shaped to approximate contour of the dental appliance. An apical seating member is disposed upon the grasping assembly to facilitate the application of seating pressure. The grasping assembly may be removably or permanently coupled to the actuating assembly. Portions of the actuating assembly, the grasping assembly, or both the actuating and grasping assemblies may be shaped to facilitate distal, mesial, or both distal and mesial manipulation of the dental appliance.

20 Claims, 3 Drawing Sheets

VERSATILE SYSTEM FOR MANIPULATION OF DENTAL APPLIANCES

TECHNICAL FIELD OF THE INVENTION

The invention relates generally to dentistry tools and, more specifically, to a versatile and ergonomic system for manipulation of dental appliances.

BACKGROUND OF THE INVENTION

Dentistry, particularly restorative dentistry, is a demanding craft—requiring a skillful blend of structural engineering and aesthetics. Dentists must artfully construct and shape what are often very complicated restorative structures while working within the confined space of a patient's mouth. Further complicating this already challenging task are safety and sanitary requirements, ergonomic problems, and concerns about patient comfort. At its best, such work might be considered tedious. At its worst, such work might be considered nearly impossible.

As a result, a number of devices and methodologies have been developed to aid dentists in performing routine procedures. Specialized handpieces, powered tools, shielding and grasping devices are continually developed to assist in nearly every aspect of routine dentistry. Often times, however, the development of one aid may simplify a particular aspect of a procedure while complicating other aspects of the same procedure. Furthermore, there are a number of routine procedures, for which no specialized tools exist, that require dentists to utilize existing devices in an unintended fashion. Thus, restorative dentistry often relies on both specialization and improvisation.

Consider, for example, the tools and procedures involved in filling interproximal cavities. Depending upon the location and size of the filling needed, a dentist may have a very difficult time forming a filling of proper structural integrity that provides a desired aesthetic appearance and proper interproximal contact. A relatively popular method of interproximal filling relies on the use of matrix bands.

Matrix bands are small appliances that serve, essentially, as a form for interproximal fillings (especially bonded fillings) when some portion of the external tooth structure is missing or has been removed. The bands are used to restore the tooth structure to its natural contour, without having to dispose excessive bonding material to the area surrounding the filling. Matrix bands are generally formed of aluminum or some other similar semi-rigid material, and typically come in a number of sizes to match tooth and filling sizes. The bands usually have some degree of concavity, in addition to multiple degrees of curvature, to match the often asymmetrical, quasi-spherical contour of a tooth. After proper placement and seating, the matrix bands are usually held in place by some sort of matrix retainer (e.g., wedge, bi-tine ring).

Thus, once a matrix band is in place, the filling procedure is significantly simplified. The proper placement and seating of a matrix band is, however, no trivial task. It is, in fact, a task that appears to be widely recognized as difficult and involved—and one for which conventional apparatus and methods are not properly adapted.

Conventionally, matrix bands have been placed using only the dentist's fingers, or placed by simple tweezers, straight pliers, or even cotton pliers. These conventional methods share a number of common problems and challenges, and each individual method presents its own unique problems and concerns.

One primary concern is maintaining the integrity of the matrix band itself. Until properly placed, the band is highly susceptible to bending and crimping. This can lead to unacceptable deformities in the band, requiring removal and placement of a new band, or acceptance of a structurally or aesthetically inferior filling.

Even the most nimble of dentists, with the daintiest of fingers, may have difficulty working within the limited space of a patient's mouth to properly place a matrix band without deforming the band. The location of the required filling can further complicate the procedure. The further posterior the required filling is (e.g., between molars), or if the filling is on the mesial surface of a tooth, the more difficult it is to manually place the small, flexible matrix bands. Furthermore, placement by finger may be much more difficult for dentists with larger hands.

Conventional placement methods typically require a great deal of manipulation at ergonomically awkward angles for a dentist. That ergonomically improper manipulation might, over time, lead to degenerative neuromuscular problems. Furthermore, if there is strong interproximal contact between the teeth, the dentist must either ply the teeth apart, such that the instrument used to ply the teeth apart does not impede the placement of the band, or break interproximal contact, in order to place the band without deforming it. Breaking interproximal contact may require removal of an excessive (i.e., unacceptable) amount of tooth structure, however, especially where only a small filling is required.

Although some conventional methods of matrix band placement utilize conventional, general-purpose instruments (e.g., conventional tweezers and pliers)—thereby reducing some of the problems associated with working in the confined space of a patient's mouth—extensive instrument manipulations, ergonomic challenges, and increased potential for damage to the band remain problematic. Using such conventional instruments may still be difficult for posterior placements. Furthermore, such general-purpose instruments are typically unsuitable for firmly grasping and manipulating the curved matrix bands without deformation. Most such instruments have flat, planar grasping surfaces that can bend or damage a matrix band. The grasping surfaces themselves are generally not arcuate in nature, and thus will not tightly grasp a significant cross section of a matrix band without deformation. Finally, most such conventional instruments are not curved or angled to provide reliable matrix band disposition in both distal and mesial orientations. Thus, placement with such conventional instruments is often tedious, time-consuming, and not possible with existing instruments.

SUMMARY OF THE INVENTION

Thus, a system that provides easy and reliable placement and removal of specially contoured dental appliances, such as matrix bands, in an ergonomically proper manner, readily usable for both distal and mesial manipulations, is now needed. This system should provide dentists with a tool that simplifies restorative procedures without deforming or damaging the appliances being placed. The system should thus provide relief from problems associated with conventional methods and apparatus.

Comprehending this, the present invention provides a versatile system for the efficient manipulation of specially contoured dental appliances, especially matrix bands. The present invention provides a shaped grasping member assembly for grasping the dental appliance. The grasping members may be angled or curved in either a convex or concave orientation, such that their angulation or curvature closely approximates the contour of the appliance(s) to be placed, and such that the angulation or curvature may be employed to facilitate manipulations in distal, mesial, or both mesial and distal orientations. The member, or members, on one side of the assembly may include an apical seat disposed along an upper edge, to secure the appliance in place and assist in applying seating pressure to the appliance.

The present invention also provides an actuating assembly, to which the grasping member assembly may be permanently or temporarily attached, such that the attachment may further facilitate placements in distal, mesial, or both mesial and distal orientations.

BRIEF DESCRIPTION OF THE DRAWINGS

For a more complete understanding of the present invention, including its features and advantages, reference is made to the following detailed description, taken in conjunction with the following drawing figures. Corresponding numerals and symbols in the different figures refer to corresponding parts unless otherwise indicated.

DETAILED DESCRIPTION OF THE INVENTION

It should be apparent to those of skill in the art, upon reference to this disclosure, that the system and teachings of the present invention are applicable to a number of dental appliances. For purposes of explanation and illustration, however, the present invention is hereafter described in reference to the handling and placement of matrix bands for use in an interproximal filling. The principles and teachings disclosed herein, however, are applicable to a wide range of dental instruments and appliances.

The present invention defines a system, comprising various structures and methods, for placing and removing matrix bands without excessive manipulation and without deforming or damaging the bands. The present invention provides a grasping member assembly, shaped in either a convex or concave orientation, to closely approximate the curvature of the matrix bands and to facilitate placement in distal, mesial, or both orientations. Certain grasping members include an apical seat disposed along an upper edge, and the grasping member assembly may be permanently or temporarily attached to a number of actuating assemblies.

Figure 1A:
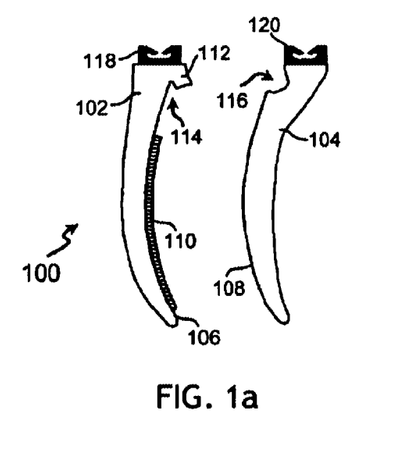
FIGS. 1a–1c illustrate an embodiment of a grasping member assembly according to the present invention.

The present invention is now described in greater detail with reference now to FIGS. 1a–1c. FIG. 1a provides a side-view, cross-sectional representation of one embodiment of a grasping member assembly 100 according to the present invention. Assembly 100 comprises first member 102 and second member 104. A matrix band is grasped between surface 106 of member 102 and surface 108 of member 104. Members 102 and 104 are formed with a matching convex longitudinal curvature. This curvature can be optimized to match the curvature of one particular size and style of matrix band, or can be generalized to closely approximate the curvatures of a number sizes and styles of matrix bands. Alternatively, members 102 and 104 may be angled, one or more times, to approximate the desired curvature(s). Surface 106 may, optionally, incorporate a traction feature 110 (e.g., scoring, small serrations, rubber padding) disposed upon, or embedded within, surface 106. Alternatively, surface 108 may incorporate feature 110. If feature 110 is utilized, it should be formed or disposed so as not to deform the matrix band during contact therewith, and should be made of a material suitable for assembly 100 (suitable materials discussed hereinafter).

Member 102 further comprises an apical seating member 112, usually disposed along the upper perimeter of surface 106. Alternatively, member 112 may be disposed further down along surface 106, or adjustably disposed along surface 106, in order to, for example, facilitate grasping matrix bands of various sizes. Generally, however, member 112 will be disposed somewhere near the top of member 102. An upper edge of a matrix band is seated against member 112, to provide stabilization during placement (or removal) and to provide a bearing point for the application of force when placing the band. As depicted in FIG. 1, member 112 comprises a contiguous appendage along member 102, forming an elongated recess 114 between member 112 and surface 106. Thus, the upper edge of the matrix band would seat within recess 114 while held by assembly 100. Alternatively, member 112 may comprise an intermittent series of short appendages forming similar recesses, or one or more simple flat shelves, or one or more post or semispherical protuberances, disposed or formed to provide the required stabilization and bearing point(s). In this embodiment, because of the curvature of members 102 and 104, member 112 is disposed along the outermost member of assembly 100. Thus, the member farthest from the tooth being filled applies bearing pressure. Member 104 may be formed with a deviation 116 to receive or accommodate member 112 while members 102 and 104 are brought together. Surface 108 is formed of a longitudinal size comparable to, but somewhat smaller than, surface 106 to allow for clearance of seating member 112 when members 102 and 104 are closed tightly together.

Members 102 and 104 further comprise attachment members 118 and 120, respectively, disposed along the upper portions thereof. Depending upon the desired actuating assembly to which members 102 and 104 will be coupled, and upon whether such coupling is intended to be permanent or temporary (i.e., removable), members 118 and 120 may be implemented in a number of ways. For example, if attachment is intended to be removable, members 118 and 120 may comprise a snap-lock or screw-on mechanism. If attachment is intended to be permanent, members 118 and 120 may comprise welds, or some or similar adjoinment, to an actuating member. Alternatively, members 102 and 104 may be formed as a contiguous, integral part of an actuating assembly, such that members 118 and 120 comprise only a transition area indistinguishable from surrounding structure.

Figure 1B:
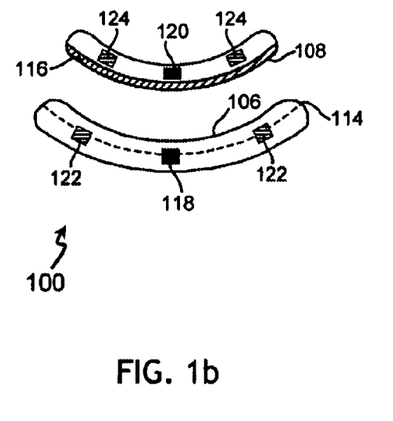

Referring now to FIG. 1b, a top view representation of assembly 100 is depicted. Members 102 and 104 are additionally formed with a matching convex lateral curvature.

This curvature can be optimized to match the curvature of one particular size and style of matrix band, or can be generalized to closely approximate the curvatures of a number sizes and styles of matrix bands. Alternatively, once again, the same effect may be achieved using one or more angulations. Although depicted as laterally larger, member 102 may be laterally larger, similar, or smaller than member 104, depending upon the desired support and manipulation characteristics of assembly 100.

Furthermore, depending upon the desired actuating assembly and the relative sizes, members 102 and 104 may comprise multiple lateral attachment members 122 and 124, respectively, in addition to or instead of members 118 and 120. Members 122 and 124 are disposed or formed so as to provide greater lateral stability across the breadth of members 102 and 104, if those members comprise a single piece. If members 102 and 104 themselves comprise multiple sub-members, then members 122 and 124 may provide individual attachment for each of the sub-members.

Figure 1C:
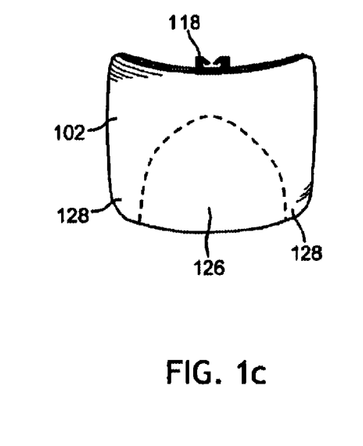

As illustrated in FIG. 1c, in a front-view representation, member 102 may comprise a single, contiguous structure. Alternatively, one or more partial aperture(s) 126 may be formed in member 102 so as to render multiple tines 128 in the lower portion of member 102. Another alternative embodiment would render member 102 as set of multiple, physically separated, polygonal or tine sub-members formed or disposed in accordance with the teachings above. All such embodiments provide a broader base of contact with the matrix band than conventional instruments (e.g., cotton pliers)—enabling a dentist to apply rotational force along the horizontal axes of the band. Although not depicted, all of these embodiments may also be implemented with member 104, and members 102 and 104 can be formed to have matching implementations, or any combination of the above-referenced embodiments.

Figure 2A:
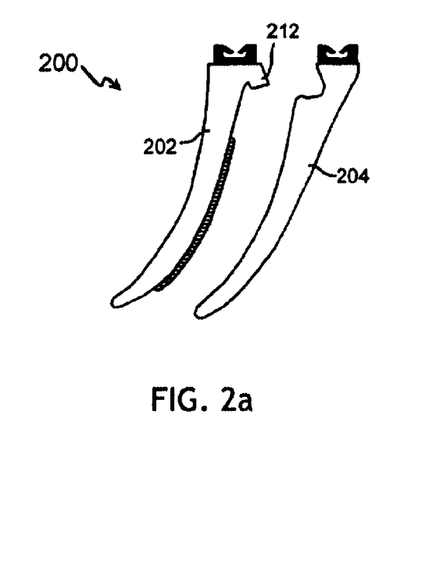
FIGS. 2a–2c illustrate another embodiment of a grasping member assembly according to the present invention.

Another embodiment of the present invention is now described with reference to FIGS. 2a–2c. FIG. 2a provides a side-view, cross-sectional representation of a grasping member assembly 200 according to the present invention. Assembly 200 and its constituent members are essentially identical to assembly 100 and its members, with the exception of curvatures (or angulations) and related orientation considerations. Members 202 and 204, which correspond to members 102 and 104, respectively, are formed with a matching concave longitudinal curvature. Again, this curvature can be optimized to match the curvature of one particular size and style of matrix band, or can be generalized to closely approximate the curvatures of a number sizes and styles of matrix bands. Apical seating member 212 is disposed along member 202, which is the innermost member of assembly 200. Thus, in this embodiment, the member closest to the tooth being filled applies bearing pressure.

Figure 2B:
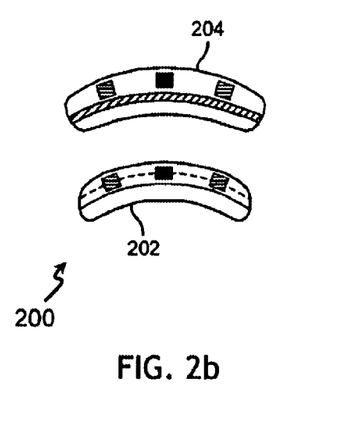

Referring now to FIG. 2b, a top view representation of assembly 200 is depicted. Members 202 and 204 are additionally formed with a matching concave lateral curvature. This curvature can be optimized to match the curvature of one particular size and style of matrix band, or can be generalized to closely approximate the curvatures of a number sizes and styles of matrix bands. Although depicted as laterally smaller, member 202 may be laterally larger, similar, or smaller than member 204, depending upon the desired support and manipulation characteristics of assembly 200.

Figure 2C:
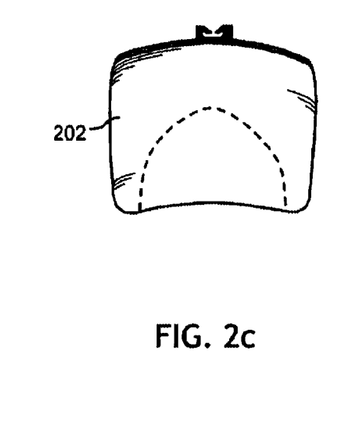

As illustrated in FIG. 2c, member 202 may comprise a single contiguous structure, a tined structured, or multiple sub-member structures (not depicted). Again, all of these embodiments are also possible with member 204, and members 202 and 204 can be formed to have matching implementations, or any combination of the above-referenced embodiments.

Although assemblies 100 and 200 have been depicted and described as comprising multiple members, other embodiments thereof may comprise only a single member. For example, it is possible that only member 102 of assembly 100 may be disposed upon some simple actuating member (e.g., a handpiece). While such an embodiment would still provide advantages over conventional methods and apparatus, it would not provide the dentist with the same ability to secure (i.e., by grasping) a matrix band for manipulation and proper placement as the multiple member embodiments do.

With the exception of the single member embodiment above, the grasping member assemblies 100 and 200 of the present invention should be coupled to, or formed as part of, some compound actuating assembly. According to the present invention, a compound actuating assembly may comprise either a bifurcated assembly (e.g., tweezers, forceps, pliers), or a stylus assembly (e.g., specialized handpiece, pneumatic drill piece), adapted to meet the requirements of the present invention. Although an almost limitless range of actuating assembly implementations are possible, the present invention requires that an actuating assembly be of a profile and length that allows adequate access to all teeth for the grasping assembly without requiring excessive manipulation by the dentist. The actuating assembly should provide sufficient pressure between the members of the grasping assembly to securely hold a matrix band. Preferably, the actuating assembly should provide the dentist with the ability to selectively adjust the grasping pressure applied.

Figure 3:
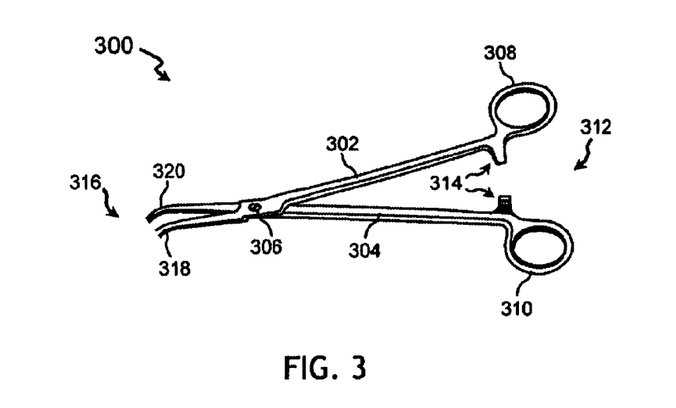
FIG. 3 illustrates an embodiment of an actuating assembly according to the present invention.

Referring now to FIG. 3, assembly 300 illustrates one embodiment of a bifurcated actuating assembly according to the present invention. Assembly 300 comprises first body member 302 and second body member 304, counter-rotationally coupled together about hinge 306. As depicted, assembly 300 comprises a scissor-style forceps assembly, having finger retainers 308 and 310 coupled to members 302 and 304, respectively, at handling end 312 of the assembly. End 312 is the end of assembly 300 that a dentist will grasp while using and manipulating it. Alternatively, members 302 and 304 may just have flat, unfinished terminations at end 312, or may have some other devices disposed in place of retainers 308 and 310 to provide grasping assistance (e.g., scored surfaces, rubber pads). Optionally, assembly 300 may further comprise a locking assembly 314 to, at a minimum, secure closure of assembly 300 and, further optionally, to provide a progression of locking pressures. As depicted in FIG. 3, assembly 314 comprises two counterposed, ratcheting hasps disposed upon members 302 and 304 that lock together progressively tighter as closing pressure is applied to members 302 and 304, and release from one another when a slight orthogonal force is applied thereto. Alternatively, assembly 314 may comprise a simple latch, a screw-type apparatus, a spring apparatus, or any other contrivance that provides the desired locking and pressure characteristics.

The other end of assembly 300 is actuating end 316. At end 316, members 302 and 304 terminate in actuating portions 318 and 320, respectively. Members of a grasping assembly may couple to, or be formed as part of, the open ends of portions 318 and 320. Portions 318 and 320 are angled or curved with respect to members 302 and 304 to provide an attached grasping assembly proper access to either distal or mesial surfaces, or both. The angles or curvatures of portions 318 and 320 are matched and aligned to provide proper closure and alignment of grasping assembly members. The curvature or angling of portions 318 and 320 enables a dentist to place a matrix band in the desired location without manipulating the entire actuating assembly to some extreme angle within a patient's mouth. Depending on whether the coupling of grasping assembly members to portions 318 and 320 is permanent or temporary, and on whether assembly 300 is intended to be used for only mesial, only distal, or both mesial and distal orientations, portions 318 and 320 may be formed with a specific or a general curvature or angling.

In one embodiment, for example, separate tools for mesial and distal orientations might be desired. Thus, two actuating assemblies are formed. Each may have grasping assemblies permanently attached thereto. The tool intended for use in mesial orientations would comprise actuating portions having a greater degree of curvature or angling than the actuating portions of the tool intended for distal orientations. Alternatively, a single tool for use in either orientation may be desired. Such a tool might have actuating portions of a generalized curvature or angle, and might rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

Finally, hinge 306 may be disposed along members 302 and 304 in a position generally biased toward end 316. This renders members 302 and 304 as relatively long lever arms, requiring minimal application of force and minimal separation of members 302 and 304 at end 312 to provide sufficient actuation of portions 318 and 320.

Figure 4:
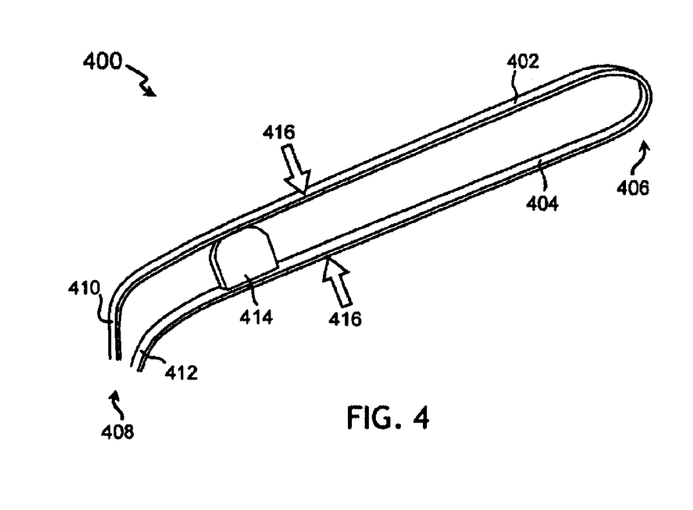
FIG. 4 illustrates another embodiment of an actuating assembly according to the present invention.

Referring now to FIG. 4, another embodiment of a bifurcated actuating assembly 400 is illustrated. Assembly 400 comprises first body member 402 and second body member 404, conjoined together as a single unit at closed end 406. The other end of assembly 400 is actuating end 408. At end 408, members 402 and 404 terminate in actuating portions 410 and 412, respectively. Members of a grasping assembly may be coupled to, or formed as part of, the open ends of portions 410 and 412.

As depicted, assembly 400 comprises a specialized tweezer-style assembly—one that brings actuating portions 410 and 412, and grasping assembly members coupled thereto, together at rest. Assembly 400 comprises a fulcrum member 414 disposed between members 402 and 404. Member 414 is disposed is a position biased towards end 408, and portions 410 and 412 are formed, such that grasping assembly members coupled to portions 410 and 412 are brought together and engaged (i.e., clamped) with maximum force when assembly 400 is not actuated. Assembly 400 is actuated by applying pressure to areas 416 along members 402 and 404, between fulcrum 414 and end 406—separating portions 410 and 412 and releasing the grasp of the grasping assembly.

Optionally, members 402 and 404 may have some devices disposed thereon, proximal to end 406, to provide grasping assistance (e.g., scored surfaces, rubber pads). Furthermore, assembly 400 may optionally comprise a locking assembly (not depicted) to, at a minimum, secure the resting closure of assembly 400. The locking assembly may comprise a latch, a hasp, a spring apparatus, or any other contrivance that provides the desired locking characteristic.

At end 408, the grasping assembly members may couple to, or be formed as part of, the open ends of portions 410 and 412. Portions 410 and 412 are angled or curved with respect to members 402 and 404 to provide an attached grasping assembly proper access to either distal or mesial surfaces, or both. The angles or curvatures of portions 410 and 412 are matched and aligned to provide proper closure and alignment of grasping assembly members. Again, the curvature or angling of portions 410 and 412 enables a dentist to place a matrix band in the desired location without manipulating the entire actuating assembly to some extreme angle within a patient's mouth. Depending on whether the coupling of grasping assembly members to portions 410 and 412 is permanent or temporary, and on whether assembly 400 is intended to be used for only mesial, only distal, or both mesial and distal orientations, portions 410 and 412 may be formed with a specific or a general curvature or angling.

In one embodiment, for example, separate tools for mesial and distal orientations might be desired. Thus, two actuating assemblies are formed. Each may have grasping assemblies permanently attached thereto. The tool intended for use in mesial orientations would comprise actuating portions having a greater degree of curvature or angling than the actuating portions of the tool intended for distal orientations. Alternatively, a single tool for use in either orientation may be desired. Such a tool might have actuating portions of a generalized curvature or angle, and might rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

Figure 5:
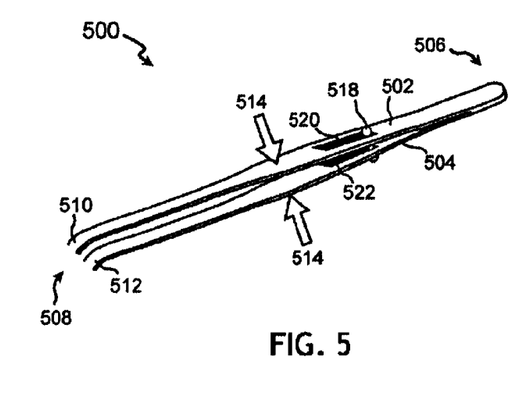
FIG. 5 illustrates another embodiment of an actuating assembly according to the present invention.

Referring now to FIG. 5, another embodiment of a bifurcated actuating assembly 500 is illustrated. Assembly 500 comprises first body member 502 and second body member 504, joined together as a single unit at closed end 506. The other end of assembly 500 is actuating end 508. At end 508, members 502 and 504 terminate in actuating portions 510 and 512, respectively. Members of a grasping assembly may be coupled to, or formed as part of, the open ends of portions 510 and 512.

As depicted, end 506 of assembly 500 comprises a conventional tweezer-style assembly—one that requires the application of closing pressure 514 somewhere along members 502 and 504 in order to bring actuating portions 510 and 512, and grasping assembly members coupled thereto, together. Thus, grasping assembly members coupled to portions 510 and 512 are brought together and engaged (i.e., clamped) with increasing force as the pressure 514 applied to assembly 500 is increased. Removing pressure 514 from assembly 500 separates portions 510 and 512 and releases the grasp of the grasping assembly. Optionally, members 502 and 504 may have some devices disposed thereon, proximal to end 506, to provide grasping assistance (e.g., scored surfaces, rubber pads).

Furthermore, assembly 500 may optionally comprise a locking assembly 516 to, at a minimum, secure closure of assembly 500 and, further optionally, to provide a progressive locking pressure. As depicted in FIG. 5, assembly 516 comprises a sliding bar member 518 disposed within apertures 520 and 522, themselves disposed within members 502 and 504, respectively. Sliding member 518 may be positioned and anchored within apertures 520 and 522 such that as it moved in the direction of end 508, members 502 and 504 are forced closer together—providing or matching pressure 514. Thus, a dentist may lock assembly 500 at a desired grasping pressure after applying closing pressure directly to members 502 and 504, or assembly 516 may be used to indirectly close assembly 500 to a desired grasping pressure before locking it in place. Pressure between grasping assembly members may be increased by moving member 518 further in the direction of end 508. Alternatively, assembly 516 may comprise a thumbwheel-type assembly that enables a dentist to indirectly close, lock, and increase the grasping pressure for, assembly 500 by turning the thumbwheel. In other embodiments, assembly 516 may comprise a simple latch, a screw-type apparatus, a spring apparatus, or any other contrivance that provides the desired locking and pressure characteristics.

At end 508, the grasping assembly members may be coupled to, or formed as part of, the open ends of portions 510 and 512. Portions 510 and 512 are angled or curved with respect to members 502 and 504 to provide an attached grasping assembly proper access to either distal or mesial surfaces, or both. The angles or curvatures of portions 510 and 512 are matched and aligned to provide proper closure and alignment of grasping assembly members. Again, the curvature or angling of portions 510 and 512 enables a dentist to place a matrix band in the desired location without manipulating the entire actuating assembly to some extreme angle within a patient's mouth. Depending on whether the coupling of grasping assembly members to portions 510 and 512 is permanent or temporary, and on whether assembly 500 is intended to be used for only mesial, only distal, or both mesial and distal orientations, portions 510 and 512 may be formed with a specific or a general curvature or angling.

In one embodiment, for example, separate tools for mesial and distal orientations might be desired. Thus, two actuating assemblies are formed. Each may have grasping assemblies permanently attached thereto. The tool intended for use in mesial orientations would comprise actuating portions having a greater degree of curvature or angling than the actuating portions of the tool intended for distal orientations. Alternatively, a single tool for use in either orientation may be desired. Such a tool might have actuating portions of a generalized curvature or angle, and rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

Figure 6:
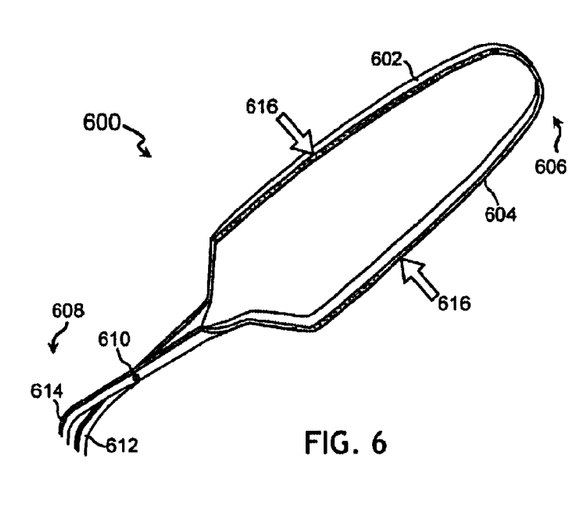
FIG. 6 illustrates another embodiment of an actuating assembly according to the present invention.

Referring now to FIG. 6, assembly 600 illustrates another embodiment of a bifurcated actuating assembly according to the present invention. Assembly 600 comprises first body member 602 and second body member 604, conjoined together as a single unit at closed end 606. The other end of assembly 600 is actuating end 608. Assembly 600 further comprises hinge 610, disposed along members 602 and 604 proximal to end 608, and about which members 602 and 604 are counter-rotationally coupled together. At end 608, members 602 and 604 terminate in actuating portions 612 and 614, respectively. Members of a grasping assembly may be coupled to, or formed as part of, the open ends of portions 612 and 614.

As depicted, assembly 600 comprises a specialized scissor-style assembly—one that brings actuating portions 612 and 614, and grasping assembly members coupled thereto, together at rest. Assembly 600 is configured, and portions 612 and 614 are formed, such that grasping assembly members coupled to portions 612 and 614 are brought together and engaged (i.e., clamped) with maximum force when assembly 600 is not actuated. Assembly 600 is actuated by applying pressure to areas 616 along members 602 and 604, between hinge 610 and end 606—separating portions 612 and 614 and releasing the grasp of the grasping assembly.

Optionally, members 602 and 604 may have some devices disposed thereon, proximal to end 606, to provide grasping assistance (e.g., scored surfaces, rubber pads). Furthermore, assembly 600 may optionally comprise a locking assembly (not depicted) to, at a minimum, secure the resting closure of assembly 600. The locking assembly may comprise a latch, a hasp, a spring apparatus, or any other contrivance that provides the desired locking characteristic.

At end 608, the grasping assembly members may couple to, or be formed as part of, the open ends of portions 612 and 614. Portions 612 and 614 are angled or curved with respect to members 602 and 604 to provide an attached grasping assembly proper access to either distal or mesial surfaces, or both. The angles or curvatures of portions 612 and 614 are matched and aligned to provide proper closure and alignment of grasping assembly members. Again, the curvature or angling of portions 612 and 614 enables a dentist to place a matrix band in the desired location without manipulating the entire actuating assembly to some extreme angle within a patient's mouth. Depending on whether the coupling of grasping assembly members to portions 612 and 614 is permanent or temporary, and on whether assembly 600 is intended to be used for only mesial, only distal, or both mesial and distal orientations, portions 612 and 614 may be formed with a specific or a general curvature or angling.

In one embodiment, for example, separate tools for mesial and distal orientations might be desired. Thus, two actuating assemblies are formed. Each may have grasping assemblies permanently attached thereto. The tool intended for use in mesial orientations would comprise actuating portions having a greater degree of curvature or angling than the actuating portions of the tool intended for distal orientations. Alternatively, a single tool for use in either orientation may be desired. Such a tool might have actuating portions of a generalized curvature or angle, and might rely on temporary attachment of, for example, grasping assembly 100 for mesial orientation and grasping assembly 200 for distal orientation. In still another alternative embodiment, a tool may comprise actuating portions of adjustable or deformable curvature or angling, allowing a dentist to select his own orientation based on the procedure to be completed.

Figure 7:
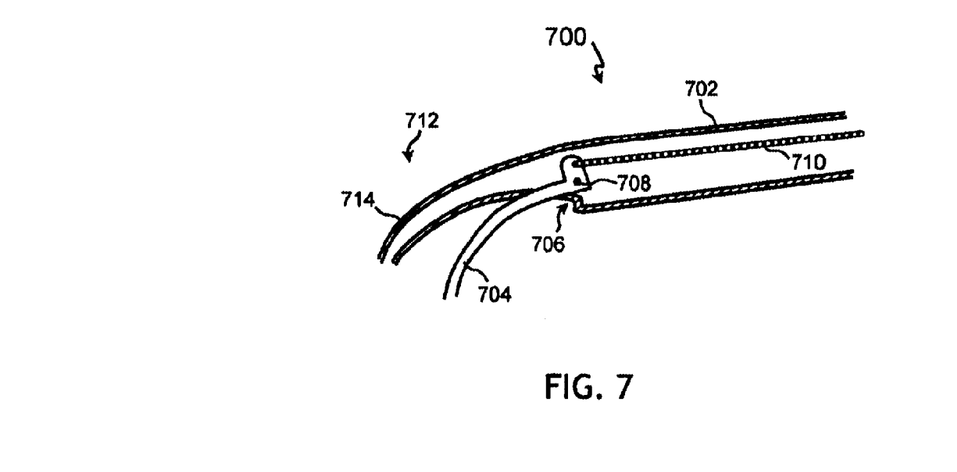
FIG. 7 illustrates another embodiment of an actuating assembly according to the present invention.

As an alternative to the bifurcated assemblies described above, the compound actuating assembly of the present invention may be implemented in a variety of stylus-type embodiments. Referring now to FIG. 7, assembly 700 illustrates one embodiment of a stylus actuating assembly according to the present invention. Assembly 700 comprises a first body member 702 and second body member 704. Member 704 may be coupled, either internally or externally, to member 702, within a recessed portion 706 of member 702 by a hinge assembly 708. A closure mechanism 710 within member 702 is operatively associated with member 704.

Member 704 is coupled to member 702 close to actuating end 712 of assembly 700. At end 712, member 702 terminates in actuating portion 714. Members of a grasping assembly may be coupled to, or formed as part of, the open ends of member 704 and portion 714.

As depicted, activation of mechanism 710 will cause member 704 to rotate about hinge 708, bringing actuating portion 714 and member 704, and grasping assembly members coupled thereto, together. Thus, grasping assembly members coupled to portion 714 and member 704 are brought together and engaged (i.e., clamped) with increasing force as the force applied by mechanism 710 is increased. Mechanism 710 may comprise a simple, finger-activated, mechanical trigger assembly, an electromechanical solenoid, a pneumatically activated solenoid, or any other similar contrivance enabling a dentist to apply a fixed or progressive range of closing pressures to member 704. Removing or reversing the closing pressure applied to member 704 will separate member 704 from portion 714, releasing the grasp of the grasping assembly. Assembly 700 may, optionally, comprise a locking apparatus or assembly of the types previously described, such that mechanism 710, member 704, or both may be locked into a desired position.

At end 712, grasping assembly members may couple to, or be formed as part of, the open ends of portion 714 and member 704. Portion 714 and member 704 are angled or curved with respect to member 702 to provide an attached grasping assembly proper access to either distal or mesial surfaces, or both. The angles or curvatures of portion 714 and member 704 are matched and aligned to provide proper closure and alignment of grasping assembly members. Again, the curvature or angling of portion 714 and member 704 enables a dentist to place a matrix band in the desired location without manipulating the entire actuating assembly to some extreme angle within a patient's mouth. Depending on whether the coupling of grasping assembly members to portion 714 and member 704 is permanent or temporary, and on whether assembly 700 is intended to be used for only mesial, only distal, or both mesial and distal orientations, portion 714 and member 704 may be formed with a specific or a general curvature or angling.

In one embodiment, for example, separate tools for mesial and distal orientations might be desired. Thus, two actuating assemblies are formed. Each may have grasping assemblies permanently attached thereto. The tool intended for use in mesial orientations would comprise portion 714 and member 704 having a greater degree of curvature or angling than portion 714 and member 704 of the tool intended for distal orientations. Alternatively, a single tool for use in either orientation may be desired. Such a tool might have portion 714 and member 704 of a generalized curvature or angle, and might rely on temporary attachment of, for example, grasping assembly 100 for mesial orientation and grasping assembly 200 for distal orientation. In still another alternative embodiment, a tool may comprise portion 714 and member 704 of adjustable or deformable curvature or angling, allowing a dentist to select his own orientation based on the procedure to be completed.

Figure 8A:
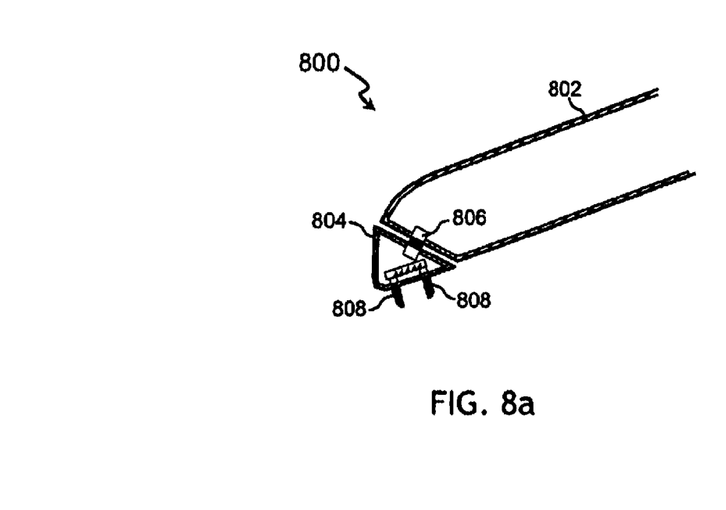
FIGS. 8a and 8b illustrates another embodiment of an actuating assembly according to the present invention.

Referring now to FIG. 8*a*, another embodiment of a stylus assembly 800 is illustrated; Assembly 800 comprises a first body member 802 and second body member 804. Members 802 and 804 are inter-connectively coupled together by intermediary member 806. Actuating members 808 are disposed upon or within member 804, and are adapted to couple with and actuate members of a grasping assembly (not shown). Members of a grasping assembly may be coupled to, or formed as part of, the open ends of members 808. Member 806 may provide a conduit from member 802 to member 804 through which a closure mechanism (not shown) may be operatively coupled to members 808. Such a closure mechanism may comprise any suitable mechanical, electromechanical, or pneumatic contrivance (e.g., pneumatic solenoid) operable to allow a dentist, while handling member 802, to engage and disengage members 808 as desired. Thus, grasping assembly members coupled to members 808 are brought together and engaged (i.e., clamped) with increasing force as the force applied by the closure mechanism is increased. Removing or reversing the force applied will separate members 808, releasing the grasp of the grasping assembly.

Figure 8B:
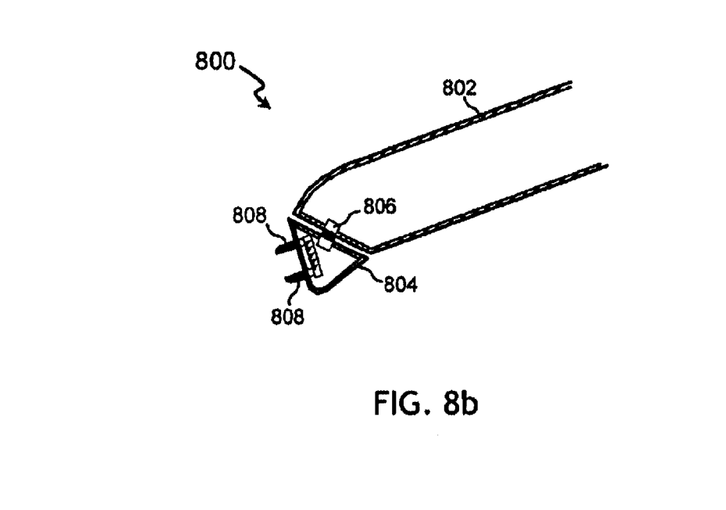

In addition or alternatively to serving as a conduit, member 806 may serve as a pivot, about which member 804 may be rotated or otherwise translated, with respect to member 802, to provide an attached grasping assembly proper access to either distal or mesial surfaces, or both. This is illustrated in FIG. 8*b*, where the rotation of member 804 changes the angle of members 808 with respect to member 802. In this example, the orientation of FIG. 8*a* might be preferable for mesial procedures and the orientation of FIG. 8*b* might be preferable for distal procedures. Alternatively, or in addition to its rotation, member 804 may be formed with an asymmetry (e.g., quasi-pyramidal or quasi-spherical) such that the rotation of member 804 further enhances bias of assembly 800 to either distal or mesial orientations. In other alternative embodiments, certain members (e.g., member 806) may be adjustable or deformable with respect to other members to achieve the desired effect. In still other alternative embodiments, multiple rotational and pivotal members of parallel and orthogonal orientation may be utilized to render the desired result. All such embodiments are configured to enable a dentist to place a matrix band in a desired location without manipulating the entire actuating assembly to some extreme angle within a patient's mouth.

For all embodiments, selection of materials for formation of the assemblies will depend on a number of factors. In all cases, materials selected must be durable enough to withstand the pressures (e.g., grasping, closing, pulling) applied throughout the system during a procedure. Furthermore, the materials utilized should be malleable enough to be formed into the desired shapes and orientations. If an embodiment requires a deformable member, the material used to form that member should be flexible enough to provide the desired deformation while remaining durable enough to withstand the pressures applied. If an assembly or a sub-portion thereof is intended to be of a disposable, one-use nature, then a reliable but inexpensive material (e.g., plastic) may be used in production. If an assembly or a member is intended to be of a re-usable nature, then a durable material (e.g., stainless steel), capable of withstanding repeated sterilization procedures, should be used in production.

While the invention has been described in reference to illustrative embodiments, the description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A dental instrument comprising:
   an actuating assembly; and
   a grasping assembly, coupled to the actuating assembly, having a grasping surface, substantially the entire area of which is adapted to conform to the curvature of a dental appliance;
   wherein a member of the actuating assembly or the grasping assembly is adapted for performing manipulation of the dental appliance along the distal, mesial, or both distal and mesial surfaces of a tooth.

2. The instrument of claim 1, wherein the grasping assembly comprises a plurality of members, each having a grasping surface.

3. The instrument of claim 2, wherein the members are angled to approximate the curvature of the dental appliance.

4. The instrument of claim 2, wherein the members are curved to approximate the curvature of the dental appliance.

5. The instrument of claim 4, wherein the members are curved concavely.

6. The instrument of claim 4, wherein the members are curved convexly.

7. The instrument of claim 2, wherein a first of the members comprises an apical seat disposed along an upper edge of its grasping surface.

8. The instrument of claim 2, wherein one of the members comprises a traction feature disposed upon its grasping surface.

9. The instrument of claim 2, wherein a portion of the actuating assembly is angled to facilitate exclusively mesial manipulation of the dental appliance.

10. The instrument of claim 2, wherein a portion of the actuating assembly is curved to facilitate exclusively mesial manipulation of the dental appliance.

11. The instrument of claim 2, wherein a portion of the grasping assembly is angled to facilitate exclusively distal manipulation of the dental appliance.

12. The instrument of claim 2, wherein a portion of the grasping assembly is curved to facilitate exclusively distal manipulation of the dental appliance.

13. The instrument of claim 2, wherein a portion of the actuating assembly is formed to selectively facilitate mesial or distal manipulation of the dental appliance.

14. The instrument of claim 1, wherein the grasping assembly is removably coupled to the actuating assembly.

15. The instrument of claim 1, wherein the grasping assembly is permanently coupled to the actuating assembly.

16. The instrument of claim 1, wherein the grasping assembly is formed as part of the actuating assembly.

17. The instrument of claim 1, wherein the actuating assembly is a bifurcated actuating assembly.

18. The instrument of claim 1, further comprising a locking assembly disposed along the actuating assembly.

19. A dental instrument, adapted to facilitate distal, mesial, or both distal and mesial manipulation of a dental appliance, comprising:

a grasping assembly, having a grasping surface shaped to approximate curvature of the dental appliance, and having an apical seating member disposed along an upper edge of the grasping surface; and an actuating assembly, operatively coupled to the grasping assembly.

20. A matrix band placement apparatus, adapted to facilitate distal, mesial, or both distal and mesial matrix band manipulation, comprising:

a first grasping member, having a first surface shaped to approximate curvature of a matrix band, having an apical seating member disposed along an upper edge of the first surface;

a second grasping member, having a first surface shaped to approximate curvature of a matrix band and shaped to cooperatively engage with the first surface of the first grasping member; and a compound actuating assembly, operatively coupled to the first and second grasping members, adapted to cooperatively engage the first and second grasping members, having a locking assembly disposed and adapted to secure engagement of the first and second grasping members.

* * * * *